United States Patent
Tipton

[11] Patent Number: 5,827,307
[45] Date of Patent: Oct. 27, 1998

[54] DISPOSABLE HEMOSTATIC CURETTE

[76] Inventor: Clyde C. Tipton, 230 Colima Ct. #913, Ponte Vedra Beach, Fla. 32082

[21] Appl. No.: 788,557

[22] Filed: Jan. 24, 1997

[51] Int. Cl.$^6$ ..................................................... A61B 17/32
[52] U.S. Cl. ............................ 606/160; 606/84; 606/131; 604/3; 401/132
[58] Field of Search .................................. 606/159, 160, 606/161, 167, 79, 131, 84; 128/757; 604/3; 401/132, 133, 134

[56] References Cited

U.S. PATENT DOCUMENTS

| | | | |
|---|---|---|---|
| 1,983,601 | 12/1934 | Conn | 604/22 |
| 2,746,461 | 5/1956 | Bocchino | 132/74.5 |
| 5,098,297 | 3/1992 | Chari et al. | 433/215 |
| 5,116,346 | 5/1992 | Yeh | 606/131 |
| 5,250,061 | 10/1993 | Michelson | 606/160 |

*Primary Examiner*—Michael Powell Buiz
*Assistant Examiner*—David O. Reip
*Attorney, Agent, or Firm*—Donald J. Ersler

[57] ABSTRACT

A disposable hemostatic curette includes a handle, at least one scraping implement, and a crushable applicator. The handle has a first end, a second end, and a length. The cross section and length of the handle are sized to facilitate easy manipulation with a thumb and forefinger. The first end of the handle is tapered to a smaller diameter which is connected to a scraping implement. The scraping implement is preferably round in shape with a shallow bore. A scraping edge of the scraping implement is a sharp edge which is formed from the inner wall of the shallow bore and a tapering outer wall of the scraping implement. A deep bore is formed in the second end of the handle, and is sized to firmly receive the outside diameter of a crushable applicator. The crushable applicator includes a transparent flexible housing, an applicator swab, and a crushable ampule containing a hemostatic solution. At least one crush window is disposed at the second end of the handle. The crush window is an opening through the second end of the handle to the deep bore disposed in thereof. The crush window is sized to allow a thumb and forefinger to break the crushable ampule located inside the crushable applicator which wets the applicator swab.

11 Claims, 1 Drawing Sheet

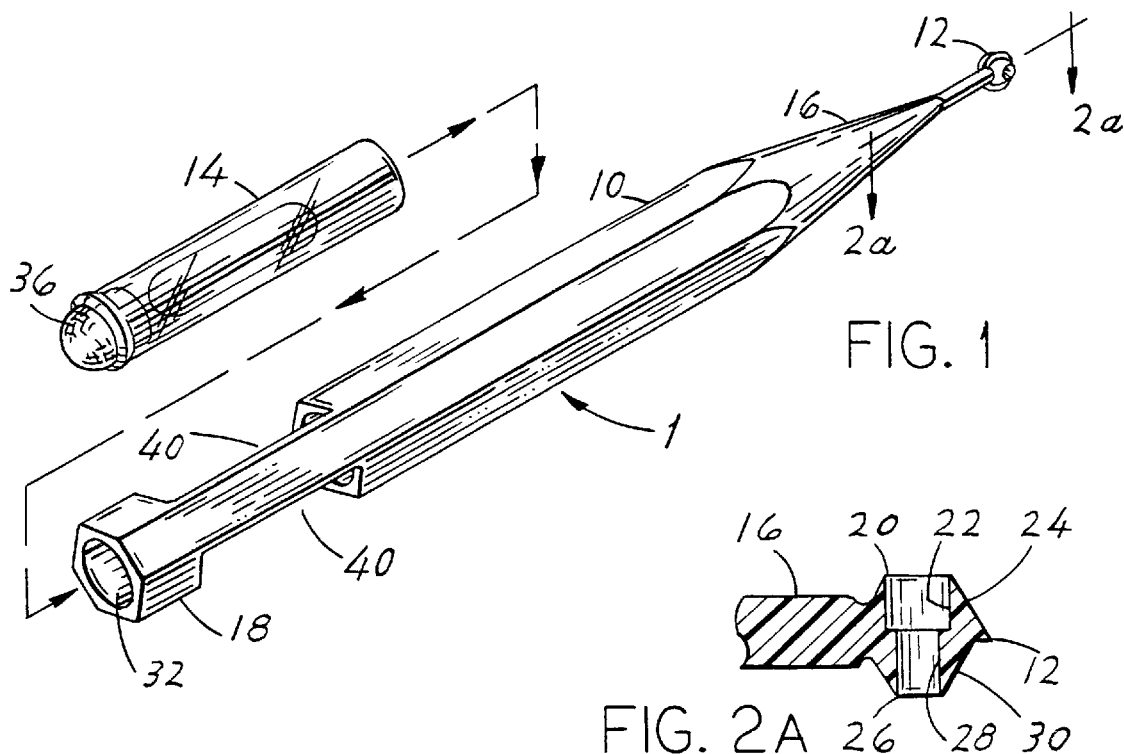
FIG. 1
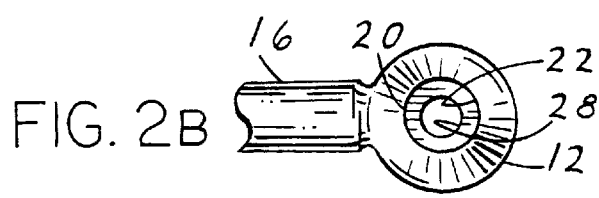
FIG. 2A
FIG. 2B
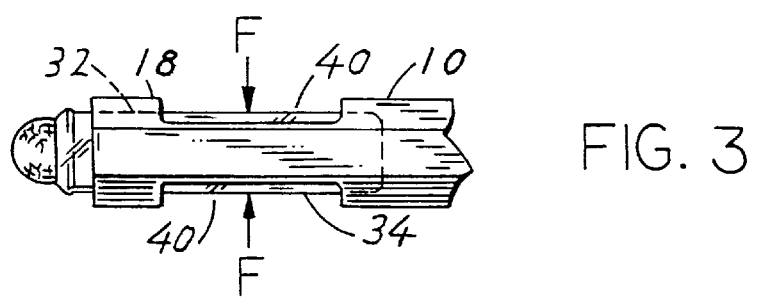
FIG. 3
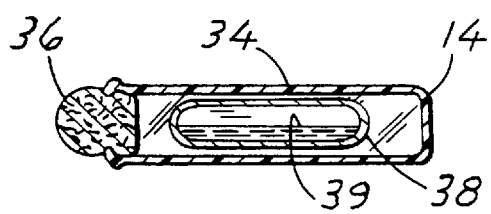
FIG. 4

DISPOSABLE HEMOSTATIC CURETTE

BACKGROUND OF THE INVENTION

1. Field of the Invention

The present invention relates generally to curettes for scraping tissue and more specifically to a disposable hemostatic curette which is sterilized for immediate use, has the convenience of an applicator end for applying a hemostatic solution to stop the bleeding of tissue, and is economical to manufacture.

2. Discussion of the Prior Art

There are numerous designs and styles of curettes for scraping tissue. Some of these designs include flat blades, wire loops, thin blade scoops, and circular openings in thin metal scalpels. Unfortunately, these designs have a few drawbacks. First, the manufacture of these devices is expensive, because a metal curette must be molded or formed into a suitable handle. Secondly, corrosion may occur to the metal curette, thus rendering it unusable. Thirdly, none of the prior art curettes are adapted to stop the bleeding of abraded tissue. The bleeding must be stopped with a separate device.

Accordingly, there is a clearly felt need in the art for a disposable hemostatic curette which is economical enough to be disposable, will not corrode, has an applicator to stop bleeding, can be adapted to have a plurality of scraping edges, and is more economical than that of the prior art to manufacture.

SUMMARY OF THE INVENTION

The primary objective of the present invention is to provide a disposable hemostatic curette which is economical enough to be disposable, will not corrode, has an applicator to stop bleeding, can be adapted to have a plurality of scraping edges, and is more economical than that of the prior art to manufacture.

According to the present invention, a disposable hemostatic curette includes a handle, at least one scraping implement, and a crushable applicator. The handle has a first end, a second end, and a length. The cross section and length of the handle are sized to facilitate easy manipulation with a thumb and forefinger. The first end of the handle is tapered to a smaller diameter which is adapted to retain at least one scraping implement. The scraping implement is preferably round in shape with a shallow bore. A scraping edge of the scraping implement is a round sharp edge which is formed from the inner wall of the shallow bore and a tapering outer wall of the scraping implement.

A deep bore originates at the second end of the handle, and is sized to firmly receive the outside diameter of a crushable applicator. The crushable applicator includes a flexible housing, an applicator swab, and a crushable ampule containing a hemostatic solution. The flexible housing is preferably transparent to allow observation of the hemostatic solution. At least one crush window is disposed at the second end of the handle. The crush window is an opening through the second end of the handle to the deep bore disposed in thereof. The crush window is sized to allow a thumb and forefinger to break the crushable ampule safely contained within the flexible housing of the crushable applicator.

Accordingly, it is an object of the present invention to provide a disposable hemostatic curette which is economical to manufacture and is intended for disposal after one time use.

It is a further object of the present invention to provide a disposable hemostatic curette which will not corrode.

It is yet a further object of the present invention to provide a disposable hemostatic curette which has an applicator solution which may be applied to abraded tissue to stop bleeding, or prevent infection.

Finally, it is another object of the present invention to provide a disposable hemostatic curette which is more economical to manufacture than that of the prior art.

These and additional objects, advantages, features and benefits of the present invention will become apparent from the following specification.

BRIEF DESCRIPTION OF THE DRAWINGS

FIG. 1 is an exploded perspective view of a disposable hemostatic curette in accordance with the present invention;

FIG. 2a is a cross sectional view of a scraping implement in accordance with the present invention;

FIG. 2b is an enlarged top view of a scraping implement in accordance with the present invention;

FIG. 3 is an enlarged top view of the second end of a disposable hemostatic curette in accordance with the present invention; and FIG. 4 is a cross sectional view of a crushable applicator in accordance with the present invention.

DETAILED DESCRIPTION OF THE PREFERRED EMBODIMENTS

With reference now to the drawings, and particularly to FIG. 1, there is shown an exploded perspective view of a disposable hemostatic curette 1. The disposable hemostatic curette 1 includes a handle 10, at least one scraping implement 12, and a crushable applicator 14. The handle 10 has a first end 16, a second end 18, and a length. The cross section and the length of the handle are sized to facilitate easy manipulation with a thumb and forefinger. The first end 16 of the handle 10 is tapered to a small diameter which is connected to at least one scraping implement 12. With reference to FIGS. 2a & 2b, the scraping implement 12 is preferably round in shape with a shallow bore, but could also be parabolic or trapezoidal. A first sharp scraping edge 20 of the scraping implement 12 is formed from the inner wall of a first shallow bore 22 and a first tapering outer wall 24 of the scraping implement 12. A second sharp scraping edge 26 is also shown with a second shallow bore 28 and a second tapering outer wall 30. The scraping implement 12 can have one or more different scraping edges. The diameter of the shallow bore is in the range of 0.5 mm to 10 mm.

A deep bore 32 originates at the second end 18 of the handle 10, and is sized to firmly receive the outside diameter of a crushable applicator 14. With reference to FIG. 4, the crushable applicator 14 includes a flexible housing 34, an applicator swab 36, and a crushable ampule 38 containing a hemostatic solution 39. The flexible housing 34 is preferably transparent to allow the hemostatic solution 39 to be seen. At least one crush window 40 is disposed at the second end 18 of the handle 10. With reference to FIG. 3, the crush window 40 is an opening through the second end 18 of the handle 10 to the deep bore 32 disposed in thereof. The crush window 40 is sized to allow a thumb and forefinger to break the crushable ampule 38 located inside the crushable applicator 14. The crushable ampule 38 can be filled with any topical medicinal solution including the hemostatic solution 39, an antiseptic solution, or a combination antiseptic and hemostatic solution.

The disposable hemostatic curette 1 is utilized to obtain tissue samples by heating the patient's skin with electrodes, then abrading the skin with one of the scraping edges to obtain a tissue sample, or remove excess tissue. The tissue obtained from the skin is forced into the shallow bore of the scraping implement 12. After the sample is obtained, a thumb and forefinger are used to break the crushable ampule 38 through at least one crush window 40. The hemostatic solution 39 inside the ampule will be absorbed by the applicator swab 36. The applicator swab 36 is then applied to the abraded area to stop any bleeding that may occur.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. A disposable hemostatic curette for removing tissue samples comprising:

a handle having a first end and a second end, said handle having at least one crush window disposed at said second end thereof which creates at least one opening in a wall of said handle;

a scraping implement being disposed at said first end of said handle; and a crushable applicator being disposed at said second end of said handle.

2. The disposable hemostatic curette for removing tissue sample of claim 1, further comprising:

said handle having a deep bore originating at said second end thereof which is sized to firmly receive said crushable applicator.

3. The disposable hemostatic curette for removing tissue samples of claim 1, further comprising:

said scraping implement having at least one sharp scraping edge, which is formed from an inner wall of a shallow bore and a tapering outer wall.

4. The disposable hemostatic curette for removing tissue samples of claim 2, further comprising:

a crushable ampule being filled with a hemostatic solution, said crushable ampule being inserted into a flexible housing and said flexible housing being inserted into said deep bore of said handle; and an applicator swab being inserted into said flexible housing to retain said crushable ampule, said applicator swab adapted to absorb and apply said hemostatic solution;

whereby sufficient force may be applied with a forefinger and thumb to said flexible housing to break said crushable ampule, said hemostatic solution being absorbed by said applicator swab.

5. The disposable hemostatic curette for removing tissue samples of claim 3, wherein said crushable applicator is filled with a topical medicinal solution.

6. The disposable hemostatic curette for removing tissue samples of claim 3, wherein said shallow bore has a round shape.

7. A method for removing tissue samples with a disposable hemostatic curette, said method comprising the steps of:

(a) providing an implement with a scraping bore at a first end and a crushable ampule at a second end, said crushable ampule being filled with a topical medicinal solution and being attached to an applicator swab;

(b) scraping tissue with a scraping edge of said scraping bore;

(c) breaking said crushable ampule containing said topical medicinal solution; and (d) applying said applicator swab substantially saturated with said topical medicinal solution to abraded tissue.

8. A disposable hemostatic curette for removing tissue samples comprising:

a handle having a first end and a second end;

a scraping implement being disposed at said first end of said handle, said scraping implement having at least one sharp scraping edge, which is formed from an inner wall of a shallow bore and a tapering outer wall;

a crushable applicator being disposed at said second end of said handle;

said handle having a deep bore originating at said second end therof which is sized to firmly receive said crushable applicator; and said handle having at least one crush window disposed at said second end thereof which creates at least one opening in a wall of said deep bore.

9. The disposable hemostatic curette for removing tissue samples of claim 8, wherein said crushable applicator comprises:

a crushable ampule filled with a topical medicinal solution;

A flexible housing; and an applicator swab;

wherein said crushable ampule is inserted into said flexible housing with said applicator swab attached thereon to retain said crushable ampule, said applicator swab being adapted to absorb and apply said topical medicinal solution, and whereby sufficient force may be applied with a forefinger and thumb to said flexible housing to break said crushable ampule, said topical medicinal solution being absorbed by said applicator swab.

10. The disposable hemostatic curette for removing tissue samples of claim 9, wherein said crushable ampule is filled with a hemostatic solution.

11. The disposable hemostatic curette for removing tissue samples of claim 8, wherein said shallow bore has a round shape.

* * * * *